(12) United States Patent
Josten

(10) Patent No.: US 8,114,207 B2
(45) Date of Patent: Feb. 14, 2012

(54) MARKER SOLUTION TO BE APPLIED BY MEANS OF AN INKJET PRINTER

(75) Inventor: Andre Josten, Nürnberg (DE)

(73) Assignee: Secutech International Pte. Ltd., Singapore (SG)

( * ) Notice: Subject to any disclaimer, the term of this patent is extended or adjusted under 35 U.S.C. 154(b) by 758 days.

(21) Appl. No.: 11/885,243

(22) PCT Filed: Mar. 1, 2006

(86) PCT No.: PCT/EP2006/001863
§ 371 (c)(1),
(2), (4) Date: Oct. 6, 2008

(87) PCT Pub. No.: WO2006/092286
PCT Pub. Date: Sep. 8, 2006

(65) Prior Publication Data
US 2009/0311415 A1   Dec. 17, 2009

(30) Foreign Application Priority Data

Mar. 4, 2005 (DE) .......................... 10 2005 009 943
Mar. 18, 2005 (DE) .......................... 10 2005 012 567

(51) Int. Cl.
*C09D 11/00* (2006.01)
(52) U.S. Cl. ............... 106/31.14; 106/31.32; 106/31.53; 106/31.64; 106/31.82; 106/31.94
(58) Field of Classification Search ............... 106/31.14, 106/31.32, 31.53, 31.64, 31.82, 31.94
See application file for complete search history.

(56) References Cited

U.S. PATENT DOCUMENTS

| | | | | |
|---|---|---|---|---|
| 3,886,083 A | * | 5/1975 | Laxer | 252/301.16 |
| 5,139,812 A | * | 8/1992 | Lebacq | 427/7 |
| 6,030,657 A | * | 2/2000 | Butland et al. | 427/7 |
| 6,221,653 B1 | * | 4/2001 | Caren et al. | 435/287.2 |
| 6,558,907 B2 | * | 5/2003 | Koroulis et al. | 506/16 |
| 7,115,301 B2 | * | 10/2006 | Sheu et al. | 427/7 |
| 7,442,502 B2 | * | 10/2008 | Hirota et al. | 435/6.19 |
| 7,923,205 B2 | * | 4/2011 | Shiba et al. | 435/6.16 |
| 2002/0187263 A1 | * | 12/2002 | Sheu et al. | 427/256 |
| 2003/0186257 A1 | | 10/2003 | Bertling et al. | |
| 2003/0190407 A1 | * | 10/2003 | Bauer et al. | 427/7 |
| 2003/0229222 A1 | | 12/2003 | Kojima | |
| 2004/0054160 A1 | | 3/2004 | Pal | |
| 2005/0045063 A1 | * | 3/2005 | Niggemann et al. | 106/31.43 |
| 2008/0293052 A1 | * | 11/2008 | Liang et al. | 435/6 |
| 2011/0046205 A1 | * | 2/2011 | Kosak et al. | 514/44 R |

FOREIGN PATENT DOCUMENTS

| | | |
|---|---|---|
| EP | 0272896 A2 | 6/1988 |
| EP | 0895082 B1 | 9/2003 |
| WO | WO-01/51652 A2 | 7/2001 |
| WO | WO-02/072878 A2 | 9/2002 |
| WO | WO-03/003800 A1 | 1/2003 |
| WO | WO-2004/053161 A1 | 6/2004 |

OTHER PUBLICATIONS

"PCT Application No. PCT/EP2006/001863 International Preliminary Report on Patentability mailed Oct. 18, 2007", 8 pgs.

"PCT Application No. PCT/EP2006/001863 International Search Report mailed Jul. 3, 2006", 6 pgs.

* cited by examiner

*Primary Examiner* — Helene Klemanski

(74) *Attorney, Agent, or Firm* — Schwegman, Lundberg & Woessner, P.A.

(57) ABSTRACT

The invention relates to a marker solution which is to be applied by means of an inkjet printer and contains (i) at least one organic solvent that has a greater steam pressure than water at 20° C. and a water content of less than 50 percent (v/v), (ii) predefined first synthetically produced nucleic acids, and (iii) a nucleic acid-complexing, organic auxiliary agent as components.

46 Claims, No Drawings

SEQUENCE LISTING

<160> NUMBER OF SEQ ID NOS: 2

<210> SEQ ID NO 1
<211> LENGTH: 25
<212> TYPE: DNA
<213> ORGANISM: Artificial sequence
<220> FEATURE:
<223> OTHER INFORMATION: A synthetic oligonucleotide

<400> SEQUENCE: 1
tggagggatg atactttgcg cttgg                                         25

<210> SEQ ID NO 2
<211> LENGTH: 32
<212> TYPE: DNA
<213> ORGANISM: Artificial sequence
<220> FEATURE:
<223> OTHER INFORMATION: A synthetic 5'-6FAM- and 3'dt(C2-DABCYL)-
      labeled oligonucleotide

<400> SEQUENCE: 2
ccaagcgcaa agtatcatcc ctccaggctt gg                                 32

MARKER SOLUTION TO BE APPLIED BY MEANS OF AN INKJET PRINTER

RELATED APPLICATIONS

This application is a nationalization under 35 U.S.C. 371 of PCT/EP2006/001863, filed Mar. 1, 2006 and published as WO 2006/092286 A1, on Sep. 8, 2006, which claimed priority under 35 U.S.C. 119 to German Application No. 10 2005 009 943.2, filed Mar. 4, 2005; and German Application No. 10 2005 012 567.0, filed Mar. 18, 2005, which applications and publication are incorporated herein by reference and made a part hereof.

The invention relates to a marker solution that is suitable for the production of forgery-proof markings and can be applied with ordinary printers conventionally used in commerce and industry, e.g. inkjet printers. In particular the invention relates to a marker solution that contains at least one organic solvent with a vapor pressure higher than water at 20° C. Such marker solutions can be used in the form of inks, in particular in inkjet printers that are used industrially. They have the advantage that they dry quickly and also permit precisely defined marking on hydrophobic surfaces. The invention further relates to a method for the production of the marker solution and the use of the marker solution for the marking of objects.

A method of extracting nucleic acid from biological material is known from US 2003/0229222 A1. In that method the biological material is vigorously shaken with small particles and with a two-phase mixture of an aqueous solution containing complexing agents and quaternary ammonium salts and an organic solvent. After extraction, the nucleic acid is obtained from the aqueous phase by ethanol precipitation. The organic solvent permits efficient purification, because contaminants contained in the biological material are easily taken up in the organic solvent.

A marker solution for the forgery-proof marking of a valuable item is known from WO 03/038000 A1. The marker solution comprises an aqueous solution with single-stranded nucleic acids and glycerol and polyethylene glycol. The glycerol acts as a hygroscopic substance and permanently keeps the marking moist. This leads to a good ability of hybridization with a complementary nucleic acid that is to be used for detecting the marking. The marker solution can for example be applied by stamping. It is not suitable for use in an inkjet printer on account of the high viscosity caused by the glycerol and polyethylene glycol, as well as the resultant slow and incomplete drying.

A medium or an ink solution that contains nucleic acid is known from US 2004/0054160 A1. The medium contains between 30 and 80 vol. % of an organic solution comprising dimethylsulfoxide, ethylene glycol, formamide or a combination thereof. The medium is also suitable for stamping. Because of a reduced water content, the medium evaporates more slowly than traditional ink. Thus, the change in the composition of the ink caused by evaporation takes place more slowly, so that more constant printing results are achieved. A quick-drying medium is not disclosed by US 2004/0054160 A1.

A "bubble-jet" method of applying samples on solid supports is known from EP 0 895 082 B1. The fluid applied can contain a nucleic acid and 5 to 10 wt. % urea, 5 to 10 wt. % glycerol, 5 to 10 wt. % thiodiglycol and 1% of an acetylenic alcohol. This fluid is not quick-drying either. The glycerol causes an applied sample to remain permanently moist.

In industrially used inkjet printers, use of a quick-drying ink having an organic solvent with a higher vapor pressure than water at 20° C. is known. Owing to the slow drying, water-based inks without organic solvents are only suitable for application on absorbent materials or for use in marking processes in which a sufficiently long drying time is possible. For fast marking processes or for application on hydrophobic and/or non-absorbent surfaces, for example high-gloss surfaces or, in particular, smooth surfaces of plastics, inks based on organic solvents are required. Conventional nucleic acids can only be dissolved in such inks at low concentration, if at all. The amount of nucleic acid that can be applied with such an ink is too small for it to be detected without an amplification reaction.

The aim of the present invention is to provide a quick-drying marker solution containing nucleic acid that is suitable for application by means of a printer. In particular, with the marker solution, it should be possible to apply nucleic acid, e.g., by means of an inkjet printer, in an amount such that direct detection is possible without carrying out an amplification reaction on the marked surface. A further aim of the invention is to provide a nucleic acid-containing marking fluid whose nucleic acids, in the printed state, are directly accessible for hybridization with complementary nucleic acids.

According to the invention, a marker solution is provided for application by means of an inkjet printer, which contains as components (i) at least one organic solvent with a higher vapor pressure than water at 20° C. and a water content of less than 50% (v/v), (ii) specified first synthetically prepared nucleic acids and (iii) an organic auxiliary agent that complexes the first nucleic acids.

The present inventors recognized that by providing the auxiliary agent that complexes the first nucleic acids, it is also possible to dissolve first nucleic acids, in particular DNA, at relatively high concentration in a marker solution based on an organic solvent. It is then possible, by means of the marker solution and, e.g., an inkjet printer, to apply DNA on a surface in an amount such that it can be detected directly, i.e., without prior amplification, using an in-situ test. It was also surprisingly found that, after drying on the surface, the nucleic acids complexed with the auxiliary agent, despite the drying and despite the presence of the auxiliary agent, are in a form such that they are directly accessible for hybridization with a complementary nucleic acid present in aqueous solution. Marking produced using the marker solution according to the invention can thus be detected quickly and simply, directly on the marked surface. For detection, it is not necessary to remove the nucleic acids from the surface. Detection of the first nucleic acids thus present can for example be carried out using a method that is known from WO 01/51652 A2. The first nucleic acid preferably is a synthetically prepared nucleic acid. Precisely defined coding can be provided by this means.

It is possible to detect the marking directly on the surface by contact with dissolved complementary detection nucleic acids at the site of marking. Hybridization can be detected, e.g., based on observation of altered optical properties of the detection nucleic acids. The detection nucleic acids used can be, e.g., molecular beacons, which are applied to the marking using a pencil or a dosing device. The fluorescence of the molecular beacons, altered by hybridization, can be detected using a hand scanner. Owing to these properties, identification of the marking can be carried out easily, even by untrained personnel, in situ, i.e., without laboratory equipment.

The marker solution according to the invention has the additional advantage that it does not contain any particles that could clog a nozzle of a printhead of an inkjet printer. Another advantage of the marker solution according to the invention is that such a large amount of nucleic acid can be dissolved in the marker solution, that in addition to the specific, first nucleic acid that serves for marking, a large amount of non-specific nucleic acid can be dissolved. Accordingly, in a manner of speaking, the specific nucleic acid can be concealed in the nonspecific nucleic acid. It is then very difficult to analyze and copy the specific nucleic acid, in order to apply a forged marking. This makes the marker solution very forgery-proof. It was found that 3 wt. % nucleic acid can be dissolved in the marker solution according to the invention. Another advantage of the marker solution according to the invention is that in the dried state it is almost invisible. As a result, the place where the marking has been applied to the marked object is not immediately recognizable. The marking can only be found with great difficulty, so that it can be analyzed and possibly copied. Accordingly, very forgery-proof markings can be produced with the marker solution according to the invention.

Furthermore, the marking applied with the marker solution according to the invention adheres well especially to smooth and even hydrophobic surfaces, without the latter having to undergo a corresponding pretreatment. In addition, the organic solvent ensures good wettability of hydrophobic surfaces.

Since organic solvents like isopropanol or ethanol are usually employed in molecular biology for the precipitation of nucleic acid, it is very surprising that a comparatively large amount of DNA can be dissolved in these solvents with the aid of an auxiliary agent that complexes the first nucleic acids, for example a cationic detergent.

In order to increase the solubility in organic solvents, the first nucleic acids could also be modified. For example, methyl or cholesteryl groups could be provided on the first nucleic acids during nucleic acid synthesis or by subsequent modification. However, chemical modification of the first nucleic acids has the disadvantage of increased costs and the unwanted possibility of isolating the first nucleic acids on the basis of the modification. The method disclosed here offers the possibility of dissolving first nucleic acids at high concentrations in organic solvents, without having to rely on modification of the first nucleic acids.

It is especially advantageous if the marker solution as a whole has a higher vapor pressure than water at 20° C. This ensures even faster drying of the applied marker solution. The vapor pressure of the organic solvent or of the marker solution at 20° C. is preferably above 0.025 bar, in particular above 0.027 bar, and more preferably above 0.03 bar. The organic solvent can be methanol, ethanol, propanol, isopropyl alcohol, butanone, acetone, ethyl ether, benzene or a mixture of at least two of these solvents.

Preferably the concentration of the organic solvent in the marker solution is greater than 50% (v/v), preferably greater than 80% (v/v), in particular greater than 90% (v/v). (v/v) means (volume/volume). The higher the proportion of organic solvent in the marker solution, the quicker the marker solution dries. The concentration of water in the marker solution preferably is less than 20% (v/v), especially preferably less than 10% (v/v), and in particular less than 5% (v/v).

In one embodiment of the invention the marker solution additionally contains a dye, in particular a fluorescent dye. In this way the marking can be located more easily for identification.

It is especially favorable if the first nucleic acids in the marker solution are in single-stranded form. Then the direct detection of the first nucleic acids does not require a denaturing step. It was found, surprisingly, that the first nucleic acids are directly accessible for hybridization in the dried, printed marking. This is all the more surprising because detection takes place by hybridization in the presence of the complexing auxiliary agent, e.g. a cationic detergent, that is present in the marking and complexes the first nucleic acids. Detection of a marking produced by means of the marker solution can thus be carried out quickly and simply on the marked surface.

The first nucleic acids contained in the marking can be detected by adding a small amount of, e.g., 1 to 10 µl of an identification solution, said identification solution containing detection nucleic acids, which are complementary to the first nucleic acids. Addition can be performed, e.g., using a pen, which is brought into contact with the marking and, as a result of capillary forces, releases a small amount of the identification solution into the marking. Of course, the identification solution can also be applied to the marking by means of a pipetting device. Hybridization is preferably detected by means of complementary molecular beacons, based on the fluorescence altered by hybridization. The altered fluorescence can be detected, e.g., by means of a hand-held fluorescence scanner. In this embodiment, in-situ detection of the marking is possible without laboratory equipment and without personnel with scientific training.

To adjust the viscosity of the marker solution it can contain viscous polymers. Adjustment of viscosity may be necessary in order to adapt the marker solution to the requirements of different printheads and their nozzles. To adjust the conductivity of the marker solution it can contain charged molecules, in particular tetrabutylammonium bromide. Adjustment of conductivity may be necessary for inkjet printers in which the point of ink application is determined by deflection of an ink jet in an electric field. A particular conductivity of the marker solution must be provided to obtain the desired deflection of the ink jet at a given field strength.

The first nucleic acids can have a length of 5 to 300 nucleotides, in particular 10 to 100 nucleotides, preferably 15 to 25 nucleotides. The greater the length of the nucleic acids, the larger the quantity of codings that can be provided. At the same time, however, with increasing length, it becomes more laborious to provide error-free defined nucleic acids. The stated lengths have proved to be favorable.

The security of a marking provided by means of the marker solution can be further increased if it contains additional nucleic acids, especially if they have a similar length to the first nucleic acids. With the additional nucleic acids it is possible to conceal the first nucleic acids within a quantity of additional nucleic acids. Consequently, it is not possible to determine the sequence of the first nucleic acid and thus fake the marker solution and/or the marking applied with it.

The ratio of the amounts of the first and the additional nucleic acids is preferably at most 1:10, especially preferably at most 1:20, in particular at most 1:100. The smaller this ratio, the more forgery-proof is the marking applied using the marker solution, because it becomes more and more difficult to isolate and identify the first nucleic acids among all of the first and additional nucleic acids that are present.

The concentration of the first or of the first and of the additional nucleic acids in the marker solution is preferably above 0.1% (w/v), in particular above 1% (w/v), more preferably above 2% (w/v). A high concentration of the first nucleic acids in the marker solution facilitates amplification-free detection of the first nucleic acid in the printed marking.

In the context of the present invention, the auxiliary agent that complexes the first nucleic acids is an organic compound that binds to the first nucleic acids, and carries at least one positive charge or positive partial charge and has organic residues. The auxiliary agent can also be a polymer, carrying more than one positive charge per molecule. Typical representatives of the auxiliary agents are cationic detergents, for example quaternary ammonium compounds with various alkyl residues. The concentration of the detergent in the marker solution can be between 0.1% (w/v) and 10% (w/v), in particular between 0.5% (w/v) and 5% (w/v), preferably between 0.7% (w/v) and 3% (w/v). (w/v) signifies (weight/volume). Organic, amphiphilic compounds, such as organic amines, can also be used as auxiliary agents. Preferably, auxiliary agents such as spermidine, spermine or polylysine, which form insoluble complexes with nucleic acids in aqueous solutions, can be used.

In a preferred embodiment of the marker solution according to the invention, the cationic detergent hexadecyltrimethylammonium bromide or dodecyltrimethylammonium bromide is used as auxiliary agent. Preferably the first and the additional nucleic acids are dissolved in the marker solution at a concentration at which they would not be completely soluble in the otherwise unaltered marker solution without the auxiliary agent. The concentration of the nucleic acids in the marker solution is preferably higher by greater than a factor of 10, preferably a factor of 100 above the concentration at which they would be soluble in the otherwise unaltered marker solution without the auxiliary agent. The higher the concentration of the first and additional nucleic acids in the marker solution, the greater is the quantity of these nucleic acids that can be applied per area unit by means of an inkjet printer. The greater the quantity applied per area unit, the easier it is to detect these nucleic acids, and the more secure the marking can be made, because a quantity of first nucleic acids that is detectable offhand can be concealed in a large quantity of additional nucleic acids.

The marker solution according to the invention can be contained in a printhead of an inkjet printer, in a reservoir or in a channel.

The invention further relates to a method for the production of the marker solution according to the invention with the following steps:

a) dissolving first synthetically produced nucleic acids in an aqueous solvent or provision of first synthetically produced nucleic acids in an aqueous solvent, b) bringing the first nucleic acids into contact with an organic auxiliary agent that complexes the first nucleic acids, whereby complexes of the first nucleic acids and the auxiliary agent are formed, c) mixing the complexes with an organic solvent that has a higher vapor pressure than water at 20° C.

Preferably the contacting of the first nucleic acids with the auxiliary agent in step b) takes place by first providing a solution of the auxiliary agent, to which an aqueous solution containing the first nucleic acids is added. In this way it is possible to ensure that the auxiliary agent is present in excess during contact with the first nucleic acids, and nucleic acid complexes saturated with the auxiliary agent can form.

Mixing of the complexes with the organic solvent can also be carried out by mixing aqueous solvents containing the first nucleic acids and the auxiliary agent with the organic solvent.

Preferably the auxiliary agent and the aqueous solvent are selected so that in step "b" the complexes from first nucleic acids and auxiliary agent are precipitated. The precipitated complexes can be separated from the aqueous solvent and dissolved in the organic solvent in step "c". The precipitated complexes can be separated for example by centrifugation or by filtration. By precipitating and separating the complexes, concentration of the nucleic acids can be achieved.

Furthermore, the invention relates to a use of a marker solution, which contains as components (i) at least one organic solvent with a higher vapor pressure than water at 20° C. and a water content of less than 50% (v/v), (ii) specified first, in particular synthetically prepared, nucleic acids and (iii) an organic auxiliary agent that complexes the first nucleic acids, for the marking of a surface of an object by means of a printer, in particular an inkjet printer.

Preferably the surface is smooth and/or consists of plastic, in particular a hydrophobic plastic. The plastic can be polyethylene or polypropylene. To increase the level of security against forgery, a marking can be formed by applying the marker solution to defined areas and another solution to other areas. The other solution has the same composition as the marker solution, except that it does not contain first nucleic acids. As a result it is difficult for a forger to ascertain which of the areas contain the first nucleic acids. Moreover, the additional area can serve as a reference area during detection of the marking.

Security can be further enhanced if the other solution contains second nucleic acids, because a forger must then additionally ascertain whether the first or the second nucleic acids provide the specific coding.

For identification of a marking applied by means of the marker solution on a surface of an object, a specific hybridization of the first nucleic acids can be carried out with complementary, i.e. specific, third nucleic acids. The third nucleic acids can be designed so that properties of the third nucleic acid are altered by the hybridization. These altered properties can give rise to a signal that can be detected. For this purpose, the third nucleic acids can for example be molecular beacons. The detectable signal can for example be a color change or a change in fluorescence. The sequences and the sequence lengths of the regions of the first nucleic acids and of the third nucleic acids complementary to each other are preferably selected so that a specific hybridization is possible at room temperature. This facilitates specific detection of the marking. It is especially preferred if detection of the marking can take place in a single-step reaction, i.e. without a washing step. Such a method of detection is for example known from WO 01/51652 A2. When the marking is formed by applying the marker solution to defined areas and the other solution to other areas, during identification of the marking it is advantageous if the additional areas are also brought into contact with the third nucleic acids, in order to see that no specific hybridization takes place there. If, however, a specific hybridization does take place there, this indicates a forged marking. The security of the method against forgery can be further increased with such a procedure.

The invention is explained in more detail below with an example of application.

1) Preparation of the Marker Solution

First a solution is prepared from 27.5 g DNA comprising 2.5 g of first nucleic acid (Sequence 1=5'-tg gagggatgat actttgcgct tgg-3') and 25 g of ultrasonically sheared herring sperm DNA (Sigma, Ordering No. D3159) in 500 ml water. Stirring vigorously, this solution is added to 1500 ml of a solution containing 100 mmol/l of dodecyltrimethylammonium bromide (Sigma, Ordering No. H9151) as auxiliary agent in water. A precipitate consisting of DNA-dodecyltrimethylammonium bromide complexes forms. The precipitate is separated by filtration and, after drying at room temperature, it is taken up in 1 l ethanol. The resultant DNA-containing ethanolic solution is clear and can be used as a marker solution itself or it can be used for the preparation of other marker solutions.

2) Production of the Marking by Inkjet Printing 800 ml of the marker solution are transferred to a container, which is connected by a pipe to the printhead of a Metronic inkjet printing device (Veitshöchheim, Germany). By means of the inkjet printing device, circular markings with a diameter of approx. 2 mm are applied to a plastic film that is transported past the printhead. At a distance of approx. 5 mm from the first marking, control markings, which are produced with marker solution without first nucleic acids, are applied to the film.

3) Detection of the Marking

For identification of the marking, two weeks after printing the marking, detection solution is applied to the marking and to the control marking by means of a pen. For this, the pen is brought into contact with the marking for approx. 2 seconds. The detection solution consists of an aqueous solution containing the molecular beacon (Sequence 2=5'-6FAM-ccaagcgcaa agtatcatcc ctccaggctt gg-Dabcyl-3'), which is partially complementary to the first nucleic acids in the marking. Immediately after contact of the marking and the control marking with the pen, the fluorescence of the marking and of the control marking is determined with a hand-held fluorescence scanner from the company identif GmbH (Erlangen, Germany). The marking is identified on the basis of the increased fluorescence of the marking relative to the control marking.

The invention claimed is:

1. A marker solution for application utilizing an inkjet printer, the marker solution comprising:
   at least one organic solvent with a higher vapor pressure than water at 20° C. and a water content of less than 50% (v/v);
   specified first synthetically prepared nucleic acids; and
   an organic auxiliary agent that complexes the first nucleic acids.

2. The marker solution of claim 1, wherein the marker solution has a higher vapor pressure than water at 20° C.

3. The marker solution of claim 1 wherein the vapor pressure of the organic solvent or of the marker solution at 20° C. is higher than 0.025 bar.

4. The marker solution of claim 1 wherein the organic solvent is methanol, ethanol, propanol, isopropyl alcohol, butanone, acetone, ethyl ether, benzene or a mixture of at least two of these solvents.

5. The marker solution of claim 1 wherein the concentration of the organic solvent in the marker solution is higher than 50% (v/v).

6. The marker solution of claim 1 wherein the concentration of water in the marker solution is less than 20% (v/v).

7. The marker solution of claim 1 wherein the marker solution additionally contains a dye.

8. The marker solution of claim 1 wherein the first nucleic acids are in single-stranded form.

9. The marker solution of claim 1 wherein the marker solution contains viscous polymers for adjusting the viscosity of the marker solution, or charged molecules for adjusting the conductivity of the marker solution, or both the viscous polymers and the charged molecules.

10. The marker solution of claim 1 wherein the first nucleic acids have a length of 5 to 300 nucleotides.

11. The marker solution of claim 1 wherein the marker solution contains additional nucleic acids.

12. The marker solution of claim 11 wherein in the solution, the quantitative ratio between the first and the additional nucleic acids is at most 1:10.

13. The marker solution of claim 11, wherein the concentration of the first or of the first and of the additional nucleic acids in the marker solution is higher than 0.1% (w/v).

14. The marker solution of claim 1, wherein the auxiliary agent complexing the first nucleic acids is a detergent with one or more positive charges.

15. The marker solution of claim 14, wherein the concentration of the detergent in the marker solution is between 0.1% (w/v) and 10% (w/v).

16. The marker solution of claim 1, wherein the auxiliary agent complexing the first nucleic acids is a monomeric or polymeric amine.

17. The marker solution of claim 1 wherein the auxiliary agent is a cationic detergent.

18. The marker solution of claim 17, wherein the cationic detergent is hexadecyltrimethylammonium bromide or dodecyltrimethylammonium bromide.

19. The marker solution of claim 11, wherein the first or the additional nucleic acids form complexes with the auxiliary agent that are insoluble in aqueous solution.

20. The marker solution of claim 11, wherein the auxiliary agent is a detergent and the solubility of the first and of the additional nucleic acids in the marker solution is higher by a factor of 5 than the solubility in an identical solution without the detergent.

21. A method for the production of the marker solution of claim 1, wherein the method comprises:
 a) dissolving first synthetically produced nucleic acids in an aqueous solvent or providing first synthetically produced nucleic acids in an aqueous solvent;
 b) bringing the first nucleic acids into contact with an organic auxiliary agent that complexes the first nucleic acids, wherein complexes of the first nucleic acids and the auxiliary agent are formed; and
 c) mixing the complexes with an organic solvent that has a higher vapor pressure than water at 20° C.

22. The method of claim 21, wherein complexes that are precipitated in step b) are separated from the aqueous solvent and are dissolved in the organic solvent in step c).

23. The method of claim 21, wherein the vapor pressure of the organic solvent at 20° C. is higher than 0.025 bar.

24. The method of claim 21, wherein the organic solvent is methanol, ethanol, propanol, isopropyl alcohol, butanone, acetone, ethyl ether, benzene or a mixture of at least two of these solvents.

25. The method of claim 21, wherein the concentration of the organic solvent in the marker solution is adjusted to a value higher than 50% (v/v).

26. The method of claim 21, wherein the concentration of water in the marker solution is adjusted to a value less than 20% (v/v).

27. The method of claim 21, wherein the concentration of the auxiliary agent in the marker solution is adjusted to a value between 0.1% (w/v) and 10% (w/v).

28. The method of claim 21, wherein a dye is added to the marker solution, to the aqueous solvent or to the organic solvent.

29. The method of claim 21, wherein the first nucleic acids are in single-stranded form.

30. The method of claim 21, wherein viscous polymers for adjusting the viscosity of the marker solution and/or charged molecules for adjusting the conductivity of the marker solution are added to the marker solution, to the aqueous solvent or to the organic solvent.

31. The method of claim 21, wherein the first nucleic acids have a length of 5 to 300 nucleotides.

32. The method of claim 21, wherein additional nucleic acids are dissolved in the aqueous solvent in addition to the first nucleic acids, or additional nucleic acids are provided in the aqueous solvent in addition to the first nucleic acids.

33. The method of claim 32, wherein the quantitative ratio between the first and the additional nucleic acids is at most 1:10.

34. The method of claim 32, wherein the concentration of the first or of the first and of the additional nucleic acids in the marker solution is adjusted to a value higher than 0.1% (w/v).

35. The method of claim 21, wherein the auxiliary agent is a detergent.

36. The method of claim 35, wherein the detergent is a cationic detergent.

37. The method of claim 36, wherein the cationic detergent is hexadecyltrimethylammonium bromide or dodecyltrimethylammonium bromide.

38. The method of claim 21, wherein the auxiliary agent is a monomeric or polymeric amine.

39. The method of claim 32, wherein the auxiliary agent is a detergent and the first and additional nucleic acids are dissolved in the organic solvent at a concentration at which they would not be completely soluble in the organic solvent without the detergent.

40. A method, comprising:
 utilizing a marker solution to mark a surface of an object using a printer, wherein the marker solution includes:
 at least one organic solvent with a higher vapor pressure than water at 20° C. and a water content of less than 50% (v/v);
 specified first nucleic acids; and
 an organic auxiliary agent that complexes the first nucleic acids.

41. The method of claim 40, wherein the printer is an inkjet printer.

42. The method of claim 40, wherein the surface is smooth.

43. The method of claim 40, wherein the surface consists of hydrophobic plastic.

44. The use method of claim 43, wherein the plastic is polyethylene or polypropylene.

45. The method of claim 40, characterized in that wherein a marking is formed by applying the marker solution to defined areas and another solution to other areas, the other solution having the same composition as the marker solution, except that it does not contain any first nucleic acids.

46. The method of claim 45, wherein the other solution contains second nucleic acids.

* * * * *

UNITED STATES PATENT AND TRADEMARK OFFICE
CERTIFICATE OF CORRECTION

| | | |
|---|---|---|
| PATENT NO. | : 8,114,207 B2 | Page 1 of 1 |
| APPLICATION NO. | : 11/885243 | |
| DATED | : February 14, 2012 | |
| INVENTOR(S) | : Andre Josten | |

It is certified that error appears in the above-identified patent and that said Letters Patent is hereby corrected as shown below:

In column 7, line 61, in Claim 3, delete "1" and insert -- 1, --, therefor.

In column 7, line 64, in Claim 4, delete "1" and insert -- 1, --, therefor.

In column 8, line 1, in Claim 5, delete "1" and insert -- 1, --, therefor.

In column 8, line 4, in Claim 6, delete "1" and insert -- 1, --, therefor.

In column 8, line 6, in Claim 7, delete "1" and insert -- 1, --, therefor.

In column 8, line 8, in Claim 8, delete "1" and insert -- 1, --, therefor.

In column 8, line 10, in Claim 9, delete "1" and insert -- 1, --, therefor.

In column 8, line 16, in Claim 10, delete "1" and insert -- 1, --, therefor.

In column 8, line 18, in Claim 11, delete "1" and insert -- 1, --, therefor.

In column 8, line 20, in Claim 12, delete "11" and insert -- 11, --, therefor.

In column 8, line 63, in Claim 17, delete "1" and insert -- 1, --, therefor.

In column 10, line 27, in Claim 40, delete "using" and insert -- utilizing --, therefor.

In column 10, line 39, in Claim 44, after "The" delete "use".

In column 10, line 41, in Claim 45, after "40," delete "characterized in that".

Signed and Sealed this
Eighteenth Day of September, 2012

David J. Kappos
*Director of the United States Patent and Trademark Office*